US00PP13212P2

(12) United States Plant Patent
Verwer

(10) Patent No.: US PP13,212 P2
(45) Date of Patent: Nov. 12, 2002

(54) DAHLIA PLANT NAMED 'MELODY LATIN'

(75) Inventor: Aad W. M. Verwer, Lisse (NL)

(73) Assignee: Gebr. Verwer, Lisse (NL)

( * ) Notice: Subject to any disclaimer, the term of this patent is extended or adjusted under 35 U.S.C. 154(b) by 0 days.

(21) Appl. No.: 09/925,249

(22) Filed: Aug. 10, 2001

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Dahlia plant named 'Melody Latin', characterized by its upright, somewhat outwardly spreading and rounded plant habit; freely branching habit, full and dense plants; freely flowering habit; decorative inflorescence form with inflorescences positioned just above the foliage; yellow-colored ray florets; excellent garden performance; and excellent inflorescence longevity.

2 Drawing Sheets

BACKGROUND OF THE INVENTION

The present Invention relates to a new and distinct cultivar of Dahlia plant, botanically known as *Dahlia hybrida* and hereinafter referred to by the name 'Melody Latin'.

The new Dahlia is a product of a planned breeding program conducted by the Inventor in Lisse, The Netherlands. The objective of the breeding program is to create new compact Dahlia cultivars with freely branching growth habit, decorative inflorescence form, attractive ray floret colors, and good inflorescence longevity.

The new Dahlia originated from a cross pollination made by the Inventor in 1996 of the *Dahlia hybrida* Gallery Art Deco, disclosed in U.S. Plant Pat. No. 10,525, as the female or seed parent with the *Dahlia hybrida* cultivar München, not patented, as the male or pollen parent. The new Dahlia was discovered and selected by the Inventor as a single flowering plant within the progeny of the stated cross grown in a controlled environment in Lisse, The Netherlands, in the summer of 1997. The selection of this plant was based on its compact plant habit and attractive ray floret coloration.

Asexual reproduction of the new Dahlia by cuttings was first conducted in Lisse, The Netherlands in the spring of 1998. Asexual reproduction by cuttings has shown that the unique features of this new Dahlia are stable and reproduced true to type in successive generations.

SUMMARY OF THE INVENTION

The cultivar Melody Latin has not been observed under all possible environmental conditions. The phenotype may vary somewhat with variations in environment such as temperature, daylength, light intensity, water and nutritional status without, however, any variance in genotype.

The following traits have been repeatedly observed and are determined to be the unique characteristics of 'Melody Latin'. These characteristics in combination distinguish 'Melody Latin' as a new and distinct Dahlia:

1. Upright, somewhat outwardly spreading and rounded plant habit.

2. Freely branching habit, full and dense plants.

3. Freely flowering habit.

4. Decorative inflorescence form with inflorescences positioned just above the foliage.

5. Yellow-colored ray florets that do not fade with subsequent development.

6. Excellent garden performance.

7. Excellent inflorescence longevity.

Plants of the new Dahlia are taller than plants of the female parent, the cultivar Gallery Art Deco. In addition, plants of the new Dahlia have yellow-colored ray florets whereas plants of the cultivar Gallery Art Deco have bronze-colored ray florets.

Plants of the new Dahlia are taller, have smaller inflorescences and more ray florets per inflorescence than plants of the male parent, the cultivar München. In addition, cuttings of plants of the new Dahlia root easily whereas cuttings of plants of the cultivar München do not root easily.

Plants of the new Dahlia can be compared to plants of the cultivar Gallery Cezanne, disclosed in U.S. Plant Pat. No. 10,511. In side-by-side comparisons conducted in Lisse, The Netherlands, plants of the new Dahlia are taller, have longer internodes and larger inflorescences than plants of the cultivar Gallery Cezanne. In addition, inflorescences of plants of the new Dahlia maintain their yellow coloration with age whereas inflorescences of plants of the cultivar Gallery Cezanne turn brownish with age.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photographs on the first sheet comprises a side perspective view of a typical flowering plant of 'Melody Latin' that was about four months old.

The photograph at the top of the second sheet comprises a close-up view of typical inflorescences of 'Melody Latin'.

The photograph at the bottom of the second sheet comprises a close-up view of a typical inflorescence and inflorescence buds of 'Melody Latin'.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer and early autumn of 2000 in Lisse, The Netherlands, in an outdoor nursery and under conditions which approximate those generally used in commercial production. During the production of the plants, day temperatures ranged between 15 and 23° C. and night temperatures ranged between 10 and 15° C. Plants were pinched one time about three to four weeks after planting. Measurements and numerical values represent average of typical flowering plants that were about four months old.

Botanical classification: *Dahlia hybrida* cultivar Melody Latin.

Parentage:

*Female, or seed, parent.*—*Dahlia hybrida* cultivar Gallery Art Deco, disclosed in U.S. Plant Pat. No. 10,525.

*Male, or pollen, parent.*—*Dahlia hybrida* cultivar München, not patented.

Propagation:

*Type.*—By vegetative cuttings.

*Time to initiate roots.*—About five days at 17° C.

*Time to develop roots.*—About 14 to 17 days at 17° C.

*Root description.*—Fine, fibrous and well-branched.

*Tuber description.*—Shape: Fusiform. Clump diameter: About 15 cm. Color: Close to 199C, with anthocyanin, 59C.

Plant description:

*Appearance.*—Herbaceous flowering container or garden plant. Inverted triangle; stems mostly upright and somewhat outwardly spreading giving a rounded appearance to the plant. Freely branching, about 10 lateral branches develop after removal of terminal apex (pinching); dense and full plants.

*Crop time.*—About 60 days from planting are required to produce flowering finished plants; rapid growth rate.

*Plant height.*—About 60 cm.

*Plant width.*—About 35 cm.

*Lateral branches* (*peduncles*).—Angle: Erect to almost 45° from vertical. Strength: Strong. Length: About 5 to 15 cm. Diameter: About 8 mm. Texture: Smooth, glabrous. Color: 144A; longitudinal stripes towards the apex, 143A.

*Foliage description.*—Arrangement: Leaves opposite; leaves may be single or compound with three or five leaflets. Typically about 4 to 5 pairs of leaves per lateral stem. Shape: Ovate. Apex: Acuminate. Base: Attenuate. Margin: Serrate. Length: Single leaves: About 9 cm. Compound leaves with three leaflets: About 14 cm. Compound leaves with five leaflets: About 18 cm. Width: Single leaves: About 3.5 cm. Compound leaves with three leaflets: About 12 cm. Compound leaves with five leaflets: About 19 cm. Venation pattern: Pinnate. Texture: Smooth, glabrous; leathery. Color: Young and mature foliage, upper surface: 147A. Young and mature foliage, lower surface: 194A. Venation, upper surface: 144B. Venation, lower surface: 144C. Petiole length: Single leaves: About 1 cm. Compound leaves with three leaflets: About 2.5 cm. Compound leaves with five leaflets: About 3.5 cm. Petiole diameter: About 4 mm. Petiole color: Upper surface: 144B. Lower surface: 144A.

Inflorescence description:

*Appearance.*—Terminal inflorescence held just above the foliage on strong peduncles. Decorative inflorescence form with elongated narrowly oblong-shaped ray florets; ray florets arranged acropetally on a capitulum. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 24 days in an outdoor environment; and as cut flowers, inflorescences maintain good color and substance for about 6 days in an indoor environment.

*Quantity of inflorescences.*—One per lateral shoot, about 70 inflorescences plant develop during the growing season, summer through autumn.

*Inflorescence bud, at stage of showing color.*—Shape: Globular. Length: About 8 mm. Diameter: About 1.2 cm. Color: 1A.

*Inflorescences.*—Shape, in profile: Hemispherical. Diameter: About 10 cm. Depht (height): About 7 cm. Disc diameter: About 1.5 cm. Receptacle diameter: About 2 cm. Receptacle height: About 5 mm.

*Ray florets.*—Shape: Enlongated, narrowly oblong. Orientation: Initially upright, outer florets perpendicular to peduncle to reflexed. Apex: Acute. Base: Attenuate; short corolla tube. Margin: Entire. Aspect: Initially concave to mostly flat. Length: About 4.2 cm. Width: About 8 mm. Texture: Smooth, glabrous; satiny. Number of ray florets per inflorescence: About 175 in about 19 rows. Color: When opening, upper surface: 2A. When opening, lower surface: 2A to lighter than 2A. Fully opened, upper surface: 2A; color does not fade with subsequent development. Fully opened, lower surface: 2B; longitudinal ridges, 4C.

*Disc florets.*—Number of disc florets per inflorescence: About 29. Shape: Tubular, elongated. Apex: Five-pointed. Length: About 1.2 cm. Width: Apex: About 3 mm. Base: About 1.5 mm. Color: Immature: 156B. Mature: Apex: 9B. Mid-section: 16C. Base: 157D.

*Phyllaries.*—Quantity: One whorl of about 5 or 6 phyllaries. Shape: Ovate. Apex: Acute. Base: Attenuate. Margin: Entire. Length: About 1.1 cm. Width: About 3 mm. Texture: Smooth, satiny. Color: Upper surface: 146B. Lower surface: 146A.

*Reproductive organs.*—Androecium: Present on disc florets only. Stamen quantity: About 15 per floret. Anther length: About 5 mm. Anther color: 21A. Pollen amount: Scarce. Pollen color: 13B. Gynoecium: Present on ray and disc florets. Pistil quantity: About 15 per floret. Pistil length: About 6 mm. Stigma color: 21D. Style length: About 4 mm. Style color: 1C. Ovary color 2D.

*Seeds.*—Length: About 4 mm. Color: 200B.

Disease resistance: Resistance to pathogens common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Melody Latin', as illustrated and described.

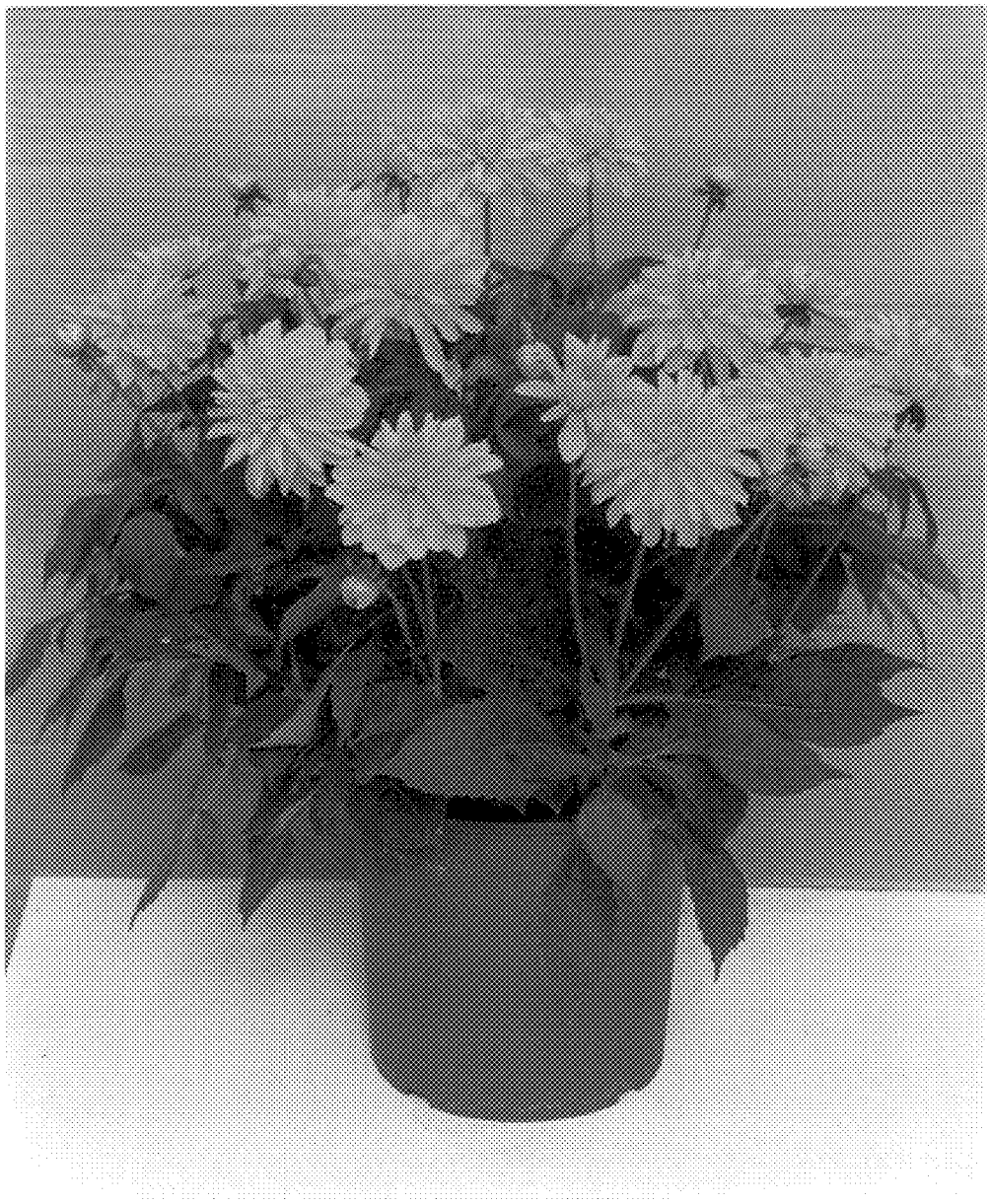

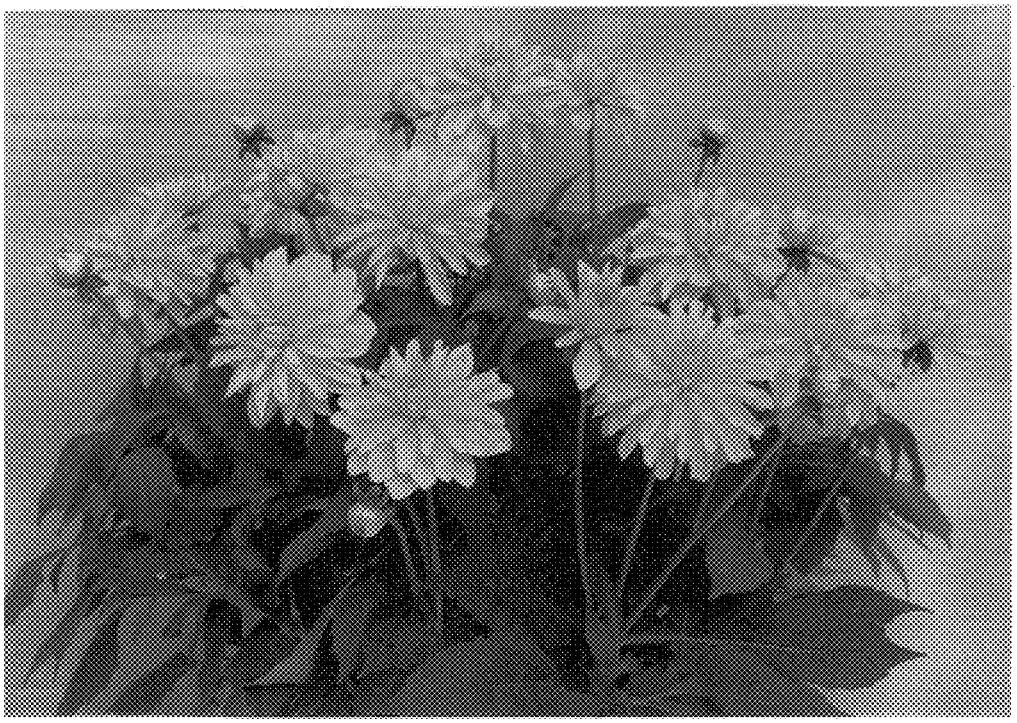
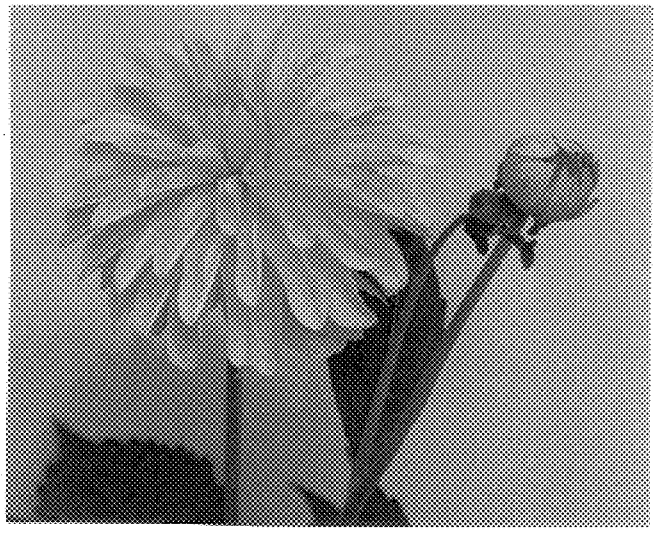

* * * * *